(12) United States Patent
Millet

(10) Patent No.: US 11,896,565 B2
(45) Date of Patent: *Feb. 13, 2024

(54) BETA-HYDROXYBUTYRATE MIXED SALT COMPOSITIONS AND METHODS OF USE

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 26 days.

This patent is subject to a terminal disclaimer.

(21) Appl. No.: 17/557,429

(22) Filed: Dec. 21, 2021

(65) Prior Publication Data

US 2022/0110895 A1 Apr. 14, 2022

Related U.S. Application Data

(60) Continuation of application No. 17/198,634, filed on Mar. 11, 2021, now Pat. No. 11,241,403, which is a continuation of application No. 16/996,509, filed on Aug. 18, 2020, now Pat. No. 10,973,786, which is a continuation-in-part of application No. 16/720,211, filed on Dec. 19, 2019, now Pat. No. 11,020,362, which is a division of application No. 16/272,145, filed on Feb. 11, 2019, now Pat. No. 10,736,861, which is a continuation-in-part of application No. 15/454,157, filed on Mar. 9, 2017, now Pat. No. 10,292,952.

(60) Provisional application No. 62/307,203, filed on Mar. 11, 2016.

(51) Int. Cl.

| A61K 31/19 | (2006.01) |
|---|---|
| A61K 31/593 | (2006.01) |
| A23L 33/12 | (2016.01) |
| A61P 3/00 | (2006.01) |
| A61K 47/14 | (2017.01) |
| A23L 33/16 | (2016.01) |
| A23L 33/175 | (2016.01) |
| A61K 9/00 | (2006.01) |
| A61K 9/02 | (2006.01) |
| A61K 9/14 | (2006.01) |
| A61K 9/20 | (2006.01) |
| A61K 9/48 | (2006.01) |
| A61K 47/10 | (2017.01) |

(52) U.S. Cl.
CPC .............. *A61K 31/19* (2013.01); *A23L 33/12* (2016.08); *A23L 33/16* (2016.08); *A23L 33/175* (2016.08); *A61K 9/006* (2013.01); *A61K 9/0019* (2013.01); *A61K 9/0053* (2013.01); *A61K 9/0095* (2013.01); *A61K 9/02* (2013.01); *A61K 9/14* (2013.01); *A61K 9/145* (2013.01); *A61K 9/2004* (2013.01); *A61K 9/2013* (2013.01); *A61K 9/4841* (2013.01); *A61K 9/4858* (2013.01); *A61K 47/10* (2013.01); *A61K 47/14* (2013.01); *A61P 3/00* (2018.01); *A23V 2002/00* (2013.01); *A23V 2200/30* (2013.01); *A23V 2250/02* (2013.01); *A23V 2250/1876* (2013.01); *A23V 2250/1878* (2013.01); *A23V 2250/1884* (2013.01)

(58) Field of Classification Search
CPC ....... A61K 31/19; A61K 31/593; A23L 33/10; A23L 33/115
USPC ....................................................... 514/167
See application file for complete search history.

(56) References Cited

U.S. PATENT DOCUMENTS

| 2,238,149 A | 4/1941 | Aeckerle |
|---|---|---|
| 2,976,073 A | 3/1961 | Russell et al. |
| 4,627,808 A | 12/1986 | Hughes |
| 4,771,074 A | 9/1988 | Lammerant et al. |
| 4,997,976 A | 3/1991 | Brunengraber et al. |
| 5,093,044 A | 3/1992 | Wretlind et al. |
| 5,100,677 A | 3/1992 | Veech |
| 5,116,868 A | 5/1992 | Chen et al. |

(Continued)

FOREIGN PATENT DOCUMENTS

| CN | 86108978 A | 11/1987 |
|---|---|---|
| CN | 1256629 A | 6/2000 |

(Continued)

OTHER PUBLICATIONS

International Preliminary Report on Patentability received for PCT Patent Application No. PCT/US2018/062093, dated Jun. 4, 2020, 6 pages.

(Continued)

*Primary Examiner* — Craig D Ricci
*Assistant Examiner* — Janet L Coppins
(74) *Attorney, Agent, or Firm* — Workman Nydegger

(57) ABSTRACT

Ketogenic compositions including a plurality of beta-hydroxybutyrate (BHB) salts are formulated to induce or sustain ketosis in a subject to which the ketogenic compositions are administered. The BHB mixed salt is formulated to provide a biologically balanced set of cationic electrolytes and avoid detrimental health effects associated with imbalanced electrolyte ratios. A ketogenic composition includes BHB salts selected from sodium, potassium, calcium, and magnesium salts. The BHB composition may also include transition metal cations (e.g., zinc or iron), one or more BHB-amino acid salts, one or more ketone precursors, supplements, or other compounds that cause a rise in blood ketone levels without adding more electrolytes to the bloodstream, a short-, medium-, or long-chain fatty acid source, vitamins, minerals, flavorants, or other excipients.

23 Claims, No Drawings

(56) References Cited

U.S. PATENT DOCUMENTS

| | | |
|---|---|---|
| 5,288,512 A | 2/1994 | Seiden |
| 5,292,774 A | 3/1994 | Hiraide et al. |
| 5,654,266 A | 8/1997 | Chen et al. |
| 5,700,670 A | 12/1997 | Yamagishi et al. |
| 6,207,856 B1 | 3/2001 | Veech |
| 6,217,915 B1 | 4/2001 | Luchansky et al. |
| 6,232,345 B1 | 5/2001 | Hiraide et al. |
| 6,316,038 B1 | 11/2001 | Veech |
| 6,323,237 B1 | 11/2001 | Veech |
| 6,380,244 B2 | 4/2002 | Martin et al. |
| 6,613,356 B1 * | 9/2003 | Vlahakos ............ A61K 9/2009 424/451 |
| 6,706,756 B1 | 3/2004 | Fitzpatrick et al. |
| 6,835,750 B1 | 12/2004 | Henderson |
| 7,351,736 B2 | 4/2008 | Veech |
| 7,807,718 B2 | 10/2010 | Hashim et al. |
| 8,101,653 B2 | 1/2012 | Veech |
| 8,124,589 B2 | 2/2012 | Henderson |
| 8,426,468 B2 | 4/2013 | Henderson |
| 8,642,654 B2 | 2/2014 | Clarke et al. |
| 8,748,400 B2 | 6/2014 | Henderson |
| 9,138,420 B2 | 9/2015 | D'Agostino et al. |
| 9,211,275 B2 | 12/2015 | Clarke et al. |
| 9,675,577 B2 | 6/2017 | D'Agostino et al. |
| 9,717,767 B2 | 8/2017 | Carpenter et al. |
| 9,795,580 B2 | 10/2017 | Weeber et al. |
| 9,808,481 B2 | 11/2017 | Ritter et al. |
| 9,925,164 B1 | 3/2018 | Hashim |
| 9,957,246 B2 | 5/2018 | Stinchcomb et al. |
| 10,022,409 B2 | 7/2018 | Carpenter et al. |
| 10,051,880 B2 | 8/2018 | Clarke et al. |
| 10,245,242 B1 | 4/2019 | Millet |
| 10,245,243 B1 | 4/2019 | Millet |
| 10,292,592 B2 | 5/2019 | Marshall et al. |
| 10,292,952 B2 * | 5/2019 | Millet ............... A61K 31/4172 |
| 10,512,615 B1 | 12/2019 | Millet |
| 10,588,876 B2 | 3/2020 | Millet |
| 10,588,877 B2 | 3/2020 | Arnold |
| 10,596,128 B2 | 3/2020 | Millet |
| 10,596,129 B2 | 3/2020 | Millet |
| 10,596,130 B2 | 3/2020 | Millet |
| 10,596,131 B2 | 3/2020 | Millet |
| 10,660,958 B2 | 5/2020 | Clarke |
| 10,736,861 B2 | 8/2020 | Millet |
| 10,792,269 B2 | 10/2020 | Hashim |
| 10,925,843 B2 * | 2/2021 | Millet ................. A61K 31/121 |
| 10,973,786 B2 | 4/2021 | Millet |
| 10,980,764 B1 | 4/2021 | D'Agostino et al. |
| 10,980,772 B2 | 4/2021 | Millet |
| 11,020,362 B2 * | 6/2021 | Millet ................. A61K 9/2013 |
| 11,103,470 B2 | 8/2021 | Millet |
| 11,241,403 B2 * | 2/2022 | Millet ................... A61K 9/006 |
| 2001/0014696 A1 | 8/2001 | Veech |
| 2001/0041736 A1 | 11/2001 | Veech |
| 2002/0013339 A1 | 1/2002 | Martin et al. |
| 2003/0022937 A1 | 1/2003 | Veech |
| 2004/0266872 A1 | 12/2004 | Veech |
| 2005/0129783 A1 | 6/2005 | McCleary et al. |
| 2007/0029913 A1 | 2/2007 | Chen |
| 2007/0135376 A1 | 6/2007 | Henderson |
| 2007/0179197 A1 | 8/2007 | Henderson |
| 2008/0058416 A1 | 3/2008 | Greenwood et al. |
| 2008/0287372 A1 | 11/2008 | Henderson |
| 2009/0253781 A1 | 10/2009 | Veech |
| 2010/0041751 A1 | 2/2010 | Henderson |
| 2010/0056631 A1 | 3/2010 | Hisamura et al. |
| 2010/0197758 A1 | 8/2010 | Andrews et al. |
| 2010/0210726 A1 | 8/2010 | Kuriyama |
| 2010/0298294 A1 | 11/2010 | Clarke et al. |
| 2011/0237666 A1 | 9/2011 | Clarke et al. |
| 2011/0287114 A1 | 11/2011 | Johnson |
| 2012/0053240 A1 | 3/2012 | Rathmacher et al. |
| 2012/0071548 A1 | 3/2012 | Veech |
| 2012/0171165 A1 | 7/2012 | Buck et al. |
| 2012/0202891 A1 | 8/2012 | Stinchcomb et al. |
| 2013/0079406 A1 | 3/2013 | Veech |
| 2013/0337116 A1 | 12/2013 | Petralia |
| 2014/0256808 A1 | 9/2014 | Henderson |
| 2014/0350105 A1 | 11/2014 | D'Agostino et al. |
| 2015/0065571 A1 | 3/2015 | Clarke et al. |
| 2015/0132280 A1 | 5/2015 | Lopez et al. |
| 2015/0320809 A1 | 11/2015 | Carpenter et al. |
| 2016/0193173 A1 | 7/2016 | Clarke et al. |
| 2016/0256411 A1 | 9/2016 | Aung-Din |
| 2017/0020844 A1 | 1/2017 | Galinski |
| 2017/0029650 A1 | 2/2017 | Veling et al. |
| 2017/0172969 A1 | 6/2017 | D'Agostino et al. |
| 2017/0258745 A1 | 9/2017 | Millet |
| 2017/0266148 A1 | 9/2017 | D'Agostino et al. |
| 2017/0290792 A1 | 10/2017 | Cavaleri |
| 2017/0296501 A1 | 10/2017 | Lowery et al. |
| 2017/0298339 A1 | 10/2017 | Hanson et al. |
| 2017/0304564 A1 | 10/2017 | Dehaan et al. |
| 2018/0021274 A1 | 1/2018 | Arnold |
| 2018/0021281 A1 | 1/2018 | Berger |
| 2018/0055797 A1 | 3/2018 | Llosa et al. |
| 2018/0057846 A1 | 3/2018 | Llosa et al. |
| 2018/0195096 A1 | 7/2018 | Veech et al. |
| 2018/0214399 A1 | 8/2018 | Spector et al. |
| 2019/0099394 A1 | 4/2019 | Ari et al. |
| 2019/0151267 A1 | 5/2019 | Millet |
| 2019/0167613 A1 | 6/2019 | Millet |
| 2019/0167614 A1 | 6/2019 | Millet |
| 2019/0177673 A1 | 6/2019 | Llosa et al. |
| 2019/0183220 A1 | 6/2019 | Takada |
| 2019/0183820 A1 | 6/2019 | Millet |
| 2019/0183821 A1 | 6/2019 | Millet |
| 2019/0191755 A1 | 6/2019 | Garvey et al. |
| 2019/0209501 A1 | 7/2019 | Tinsley, M et al. |
| 2019/0262293 A1 | 8/2019 | Millet |
| 2019/0313682 A1 | 10/2019 | Nagel |
| 2019/0321309 A1 | 10/2019 | Millet |
| 2020/0078973 A1 | 3/2020 | Valeze et al. |
| 2020/0140371 A1 | 5/2020 | Verdin et al. |
| 2020/0268701 A1 | 8/2020 | D'Agostino et al. |

FOREIGN PATENT DOCUMENTS

| | | |
|---|---|---|
| CN | 1347319 A | 5/2002 |
| CN | 101969769 A | 2/2011 |
| CN | 102164884 A | 8/2011 |
| CN | 104224823 A | 12/2014 |
| CN | 105050594 A | 11/2015 |
| CN | 106038532 A | 10/2016 |
| CN | 106459646 A | 2/2017 |
| CN | 106858066 A | 6/2017 |
| EP | 1827412 A1 | 9/2007 |
| EP | 1915144 A2 | 4/2008 |
| EP | 2283834 A2 | 2/2011 |
| EP | 2976073 A1 | 1/2016 |
| EP | 3094321 A1 | 11/2016 |
| FR | 2997302 A1 | 5/2014 |
| JP | 11-060434 A | 3/1999 |
| JP | 2002-521330 A | 7/2002 |
| JP | 2004-035417 A | 2/2004 |
| JP | 2015-042644 A | 3/2015 |
| JP | 2015-514104 A | 5/2015 |
| JP | 2016-514725 A | 5/2016 |
| JP | 2016-121128 A | 7/2016 |
| JP | 2017-046688 A | 3/2017 |
| JP | 2020-502652 A | 1/2020 |
| JP | 2020-527583 A | 9/2020 |
| JP | 2021-504476 A | 2/2021 |
| JP | 2021-506294 A | 2/2021 |
| RU | 2345546 C2 | 2/2009 |
| WO | 87/03808 A1 | 7/1987 |
| WO | 98/41200 A1 | 9/1998 |
| WO | 03/70823 A2 | 8/2003 |
| WO | 2005/107724 A1 | 11/2005 |
| WO | 2006/061624 A1 | 6/2006 |
| WO | 2007/115282 A2 | 10/2007 |
| WO | 2008/005818 A1 | 1/2008 |
| WO | 2008/021394 A2 | 2/2008 |
| WO | 2008/024408 A2 | 2/2008 |

(56) References Cited

FOREIGN PATENT DOCUMENTS

| WO | 2009/089144 A1 | 7/2009 |
|---|---|---|
| WO | 2010/021766 A1 | 2/2010 |
| WO | 2011/101171 A1 | 8/2011 |
| WO | 2013/150153 A1 | 10/2013 |
| WO | 2014/153416 A1 | 9/2014 |
| WO | 2015/071811 A1 | 5/2015 |
| WO | 2015/156865 A1 | 10/2015 |
| WO | 2016/123229 A1 | 8/2016 |
| WO | 2016/149687 A1 | 9/2016 |
| WO | 2017/156446 A1 | 9/2017 |
| WO | 2017/165443 A1 | 9/2017 |
| WO | 2017/165445 A1 | 9/2017 |
| WO | 2017/208217 A2 | 12/2017 |
| WO | 2018/055388 A1 | 3/2018 |
| WO | 2018/089863 A1 | 5/2018 |
| WO | 2018/114309 A1 | 6/2018 |
| WO | 2018/175879 A1 | 9/2018 |
| WO | 2018/187324 A1 | 10/2018 |
| WO | 2019/018683 A1 | 1/2019 |
| WO | 2019/204148 A1 | 10/2019 |
| WO | 2019/237152 A1 | 12/2019 |

OTHER PUBLICATIONS

International Preliminary Report on Patentability received for PCT Patent Application No. PCT/US2021/045186, dated Mar. 9, 2023, 7 pages.
International Preliminary Report on Patentability received for PCT Patent Application No. PCT/US2021/050302, dated Mar. 2, 2023, 8 pages.
Sorensen et al. ("Simultaneous determination of ß-hydroxybutyrate and ß-hydroxy-ß-methylbutyrate in human whole blood using hydrophilic interaction liquid chromatography electrospray tandem mass spectrometry", Clinical Biochemistry, 2013, vol. 46, pp. 1877-1883) (Year: 2013).
Optical Purity and Enantiomeric Excess at https://www.masterorganicchemistry.com/2017/02/24/optical-purity-and-enantiomeric-excess/. (Retrieved from the internet Nov. 6, 2018) (Year: 2018).
Parker, Steve, "Ketogenic Mediterraanean Diet: Version 2.3," Nov. 23, 2010, pp. 1-3. (Year: 2010).
PCT International Search Report and Written Opinion issued by the International Searching Authority dated Jul. 15, 2014 or International Patent Application No. PCT/US2014/031237.
Pete J Cox et al., "Acute nutritional ketosis: implications for exercise performance and metabolism," Extreme Physiology & Medicine, vol. 3, Issue 1, Dec. 1, 2014, pp. 1-9.
Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.
Pubchem, "Acetoacetic acid" Electronic Resource: https://pubchem.ncbi.nim.nih.gov/compound/Acetoacetic-acid, Retrieved on Sep. 3, 2019.
Robson et al. Expert Opin. Drug Saf. (2011), vol. 10, pp. 675-685 (Year: 2011).
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Sajewicz et al. in Journal of Liquid Chromatography & Related Technologies, 33:1047-1057 (2010) (Year: 2010).
Serum Ketones Test. MedlinePlus Medical Encyclopedia. Downloaded Apr. 1, 2015. http://www.nlm.nih.gov/medlineplus/ency/article/003498.htm.
Shigeno et al. in Biosci. Biotech. Biochem., 56(2), 320-323 (1992) (Year: 1992).
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
Tisdale, "Reduction of weight loss and tumour size in a cachexia model by a high fat diet", British Journal of Cancer, Jul. 1987, vol. 56, p. 39-43.
Vandenberghe et al. in Can. J. Physiol. Pharmacol. 95: 455-458 (2017) (Published at www.nrcresearchpress.com/cjpp on Nov. 25, 2016). (Year: 2016).
Veech, "The Therapeutic Implications of Ketone Bodies: The Effects of Ketone Bodies in Pathological Conditions: Ketosis, Ketogenic Diet, Redox States, Insulin Resistance, and Mitochondrial Metabolism", Prostaglandins Leukot Essent Fatty Acids, Mar. 2004, 70(3), pp. 309-319.
Veech, et al., "Ketone Bodies Mimic the Life Span Extending Properties of Caloric Restriction", IUBMB Life Feb. 8, 2017.
Vorgerd, M. and J. Zange. Treatment of glycogenosys type V (McArdle disease) with creatine and ketogenic diet with clinical scores and with 31P-MRS on working leg muscle. Acta Myologica, 2007; XXVI; pp. 61-63.
Acetoacetate, Acetone, and Dibenzylamine (A Contaminant in L-(+)-Beta-Hydroxybutyrate) Exhibit Direct Anticonvulsant Actions in Vivo, Epilepsia, Raven Press Ltd, New York, US, vol. 43, No. 4, Apr. 1, 2002 (Apr. 1, 2002), pp. 358-361.
European Search Report received for EP Patent Application No. 20755289.4, dated Oct. 11, 2022, 7 pages.
European Search Report received for EP Patent Application No. 20755994.9, dated Sep. 21, 2022, 6 pages.
European Search Report received for EP Patent Application No. 20805593.9, dated Dec. 16, 2022, 9 pages.
Extended European Search Report received for EP Patent Application No. 20755770.3, dated Sep. 1, 2022, 7 pages.
Grootaert, C. Comparison of prebiotic effects of arabinoxylan oligosaccharides and inulin in a simulator of the human intestinal microbial ecosystem, 2009, FEMS Microbiology Ecology, 69: 231-242 (Year: 2009).
Haces M L et al.: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.
Holscher, H. Dietary fiber and prebiotics and the gastrointestinal microbiota, 2017, Gut Microbes, 8(2): 172-184 (Year: 2017).
International Preliminary Report on Patentability received for PCT Patent Application No. PCT/US2021/017078, dated Aug. 18, 2022, 7 pages.
International Search Report and Written Opinion received for PCT Patent Application No. PCT/US2021/063559, dated Mar. 18, 2022, 9 pages.
John C Newman et al: "beta-Hydroxybutyrate: A Signaling Metabolite", Annual Review of Nutrition, vol. 37, Aug. 21, 2017 (Aug. 21, 2017), pp. 51-76, XP055771586.
Lile et al. Drug Alcohol Depend. 2012, 122 (1-2), 61-69.
Maguire et al., "Gut dysbiosis, leaky gut, and intestinal epithelial proliferation in neurological disorders: towards the development of a new therapeutic using amino acids, prebiotics, probiotics, and postbiotics", Rev Neurosci . Jan. 28, 2019, vol. 30, No. 2, pp. 179-201.
National Center for Biotechnology Information. PubChem Compound Summary for CID 441, 3-Hydroxybutyric acid, https://pubchem.ncbi.nlm.nih.gov/compound/3-Hydroxybutyric-acid. (Year: 2005).
Rich A.J., "Ketone Bodies as Substrates," Proceedings of the Nutrition Society (1990), vol. 49, 361-373.
Sanchez, J. I. et al. Arabinoxylan-oligosaccharides (AXOS) affect the protein/carbohydrate fermentation balance and microbial population dynamics of the Simulator of Human Intestinal Microbial Ecosystem, 2009, Microbial Biotechnology, 2(1): 101-113 (Year: 2009).
Slavin, J. Fiber and Prebiotics: Mechanisms and Health Benefits, 2013, Nutrients, 5: 1417-1425 (Year: 2013).
Stubbs et al., "On the Metabolism of Exogenous Ketones in Humans", frontiers in Physiology, vol. 8, 2017, 13 pages.
The Medical Republic, 2018, Sustained Release Sodium Butyrate Supplement Now Available to Support Management of GI Disorders, https://medicalrepublic.com.au/sustained-release-sodium-

(56) References Cited

OTHER PUBLICATIONS butyrate-supplement-now-available-support-management-gi-disorders/ 15791; newly cited (Year: 2018).

Tsai et al., "Stereoselective effects of 3-hydroxybutyrate on glucose utilization of rat cardiomyocytes" life Sciences 78(2006) pp. 1385-1391.

Walton, G, et al. A randomised, double-blind, placebo controlled cross-over study to determine the gastrointestinal effects of consumption of arabinoxylan-oligosaccharides enriched bread in healthy volunteers, 2012, Nutrition Journal, 11(36): 1-11 (Year: 2012).

Wu et al., "Medium-Chain Triglycerides in Infant Formulas and Their Relation to Plasma Ketone Body Concentrations," Pediatric Research, vol. 20, No. 4, (1986), pp. 338-341.

Yang Y. et al., Role of Adherent-Invasive *Escherichia coli* in Inflammatory Bowel Disease, Letters in Biotechnology, No. 06, Nov. 30, 2016.

Zaleski, A. et al., Butyric acid in irritable bowel syndrome, 2013, Prz Gastroenterol, 8(6), 350-353 (Year: 2013).

A New Toy Measuring Blood Ketones. Diet Doctor, Aug. 21, 2012. Downloaded Apr. 1, 2015. http://www.dietdoctor.com/a-new-toy-measuring-blood-ketoones.

Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.

Arendash et al. "Caffeine and Coffee as Therapeutics Against Alzheimer's Disease", Journal of Alzheimer's Disease 20, 2010, S117-S126.

Arnold, Instant Ketosis?, (2013), Aug. 4, 2013 (retrieved on Apr. 21, 2017), p. 1-3. Retrieved from the internet; URL: <http://patrickarnoldblog.com/instant-ketosis/. (Year: 2013).

Bastin et al., "Salt Slection and Optimisation Procedures for Pharmaceutical New Chemical Entities", American Chemical Society and The Royal Society of Chemistry, vol. 4, No. 5, 2000, pp. 427-435.

Blazquez et al. Journal of Neurochemistry, 1999, vol. 72 No. 4, pp. 1759-1768. (Year: 1999).

Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.

Craciun, S. et al. Microbial conversion of choline to trimethylamine requires a glycyl radical enzyme, 2012, PNAS, 109(52): 21307-21312 (Year: 2012).

Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).

Dietary Guidelines Recommendations at https://health.gov/our-work/food-nutrition/2015-2020-dietary-guidelines/guidelines/appendix-7/ (2010) (retrieved from the internet Oct. 20, 2020) (Year: 2010).

Dolson, Laura. How to Test Your Blood for Ketones. Downloaded Apr. 1, 2015. http://lowcarbdiets.about.com/od/KetogenicDiets/a/How-to-Test-Blood-For Ketones.htm.

Extended European Search Report issued in PCT/US2017021886 dated Oct. 17, 2019.

Extended European Search Report received for EP Patent Application No. 19788264.0, dated Dec. 20, 2021, 11 pages.

Hashim, Sarni A., et al., "Ketone body therapy: from the ketogenic diet to the oral administration of ketone ester", Journal of Lipid Research, vol. 55, 2014.

Haywood A, Glass BD. Pharmaceutical excipients—where do we begin? Australian Prescriber. 2011; 34: 112-114.

Henderson, Samuel T. "Ketone Bodies as a Therapeutic for Alzheimer's Disease." Neurotherapeutics. Jul. 2008;5(3):470-80.

Holtzman et al., "Role of adenosine receptors in caffeine tolerance", J. Pharmacol. Exp. Ther., 1991 ;256(1 ):62-68.

Ichim, T. et al., Experimental support for the effects of a probiotic/digestive enzyme supplement on serum cholesterol concentrations and the intestinal microbiome, 2016, Journal of Translational Medicine, 14(184), 1-9 (Year: 2016).

International Preliminary Report on Patentability received for PCT Patent Application No. PCT/US2020/016952, dated Aug. 26, 2021, 7 pages.

International Preliminary Report on Patentability received for PCT Patent Application No. PCT/US20/37289, dated Dec. 30, 2021, 6 pages.

International Preliminary Report on Patentability received for PCT Patent Application No. PCT/US2019/048364, dated Mar. 11, 2021, 7 pages.

International Preliminary Report on Patentability received for PCT Patent Application No. PCT/US2020/017552, dated Aug. 26, 2021, 7 pages.

International Preliminary Report on Patentability received for PCT Patent Application No. PCT/US2020/017555, dated Aug. 26, 2021, 7 pages.

International Preliminary Report on Patentability received for PCT Patent Application No. PCT/US2020/017556, dated Aug. 26, 2021, 7 pages.

International Preliminary Report on Patentability received for PCT Patent Application No. PCT/US2020/033159, dated Nov. 25, 2021, 6 pages.

International Search Report and Written Opinion issued in PCT/US19/48357 dated Nov. 18, 2019.

International Search Report and Written Opinion issued in PCT/US19/48364 dated Nov. 15, 2019.

International Search Report and Written Opinion issued in PCT/US20/16952 dated Apr. 22, 2020.

International Search Report and Written Opinion issued in PCT/US20/17552 dated May 4, 2020.

International Search Report and Written Opinion issued in PCT/US20/17556 dated May 4, 2020.

International Search Report and Written Opinion received for PCT Patent Application No. PCT/US20/017555, dated May 4, 2020, 8 pages.

International Search Report and Written Opinion received for PCT Patent Application No. PCT/US20/37289, dated Sep. 30, 2020, 8 pages.

International Search Report and Written Opinion received for PCT Patent Application No. PCT/US2020/033159, dated Aug. 12, 2020, 9 pages.

International Search Report and Written Opinion received for PCT Patent Application No. PCT/US21/045186, dated Nov. 22, 2021, 10 pages.

International Search Report and Written Opinion received for PCT Patent Application No. PCT/US21/17078, dated Apr. 23, 2021, 9 pages.

International Search Report cited in PCT/US18/62093 dated Feb. 1, 2019.

International Search Report cited in PCT/US19/27214 dated Jun. 25, 2019.

It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.

James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).

Karppanen et al, J. Human Hypertension (2005), vol. 19, pp. S10-S19. (Year: 2005).

Kesl, et al., "Effects of exogenous ketone supplementation on blood ketone, glucose, triglyceride, and lipoprotein levels in Sprague-Dawley rats", Nutrition & Metabolism (2016).

Kim Do Young et al., "Ketone bodies are protective against oxidative stress in neocortical neurons," Journal of Neurochemistry, vol. 101, Issue 5, Jun. 1, 2007, pp. 1316-1326.

Kirsch, Jr et al. "Butanediol Induced Ketosis Increases Tolerance to Hypoxia in the Mouse." Stroke. 1980, vol. 11, No. 3, pp. 506-513.

(56) References Cited

OTHER PUBLICATIONS

Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.

Krotkiewski, "Value of VLCD Supplementation with Medium Chain Triglycerides", Int J Obes Relat Metab Disord, Sep. 2001, 25(9), pp. 1393-1400.

Maalouf M et al., "Ketones inhibit mitochondrial production of reactive oxygen species production following glutamate excitotoxicity by increasing NADH oxidation," Neuroscience, New York, NY, US, vol. 145, Issue 1, Mar. 2, 2007, pp. 256-264.

Maalouf M et al., "The neuroprotective properties of calorie restriction, the ketogenic diet, and ketone bodies," Brain Research Reviews, Elsevier, NL, vol. 59, No. 2, Mar. 1, 2009, pp. 293-315.

Malo, M. S. et al., Intestinal alkaline phosphatase preserves the normal homeostasis of gut microbiota, 2010, Gut, 59, 1476-1484 (Year: 2010).

Murray, Andrew J., et al. "Novel ketone diet enhances physical and cognitive performance", The FASEB Journal, Vo. Dec. 30, 2016.

Nova Max Plus Glucose and Ketone Testing with One Monitor. Downloaded Apr. 1, 2015. http://www.novacares.com/nova-max-plus/.

Anonymous: "Blue Lemon Ice Advanced Formula", MINTEL, Database accession No. 4315637, 2016, pp. 3.

Anonymous: "Strawberry Pineapple Flavour Pre-Exertion Performance Optimizer", MINTEL, Database accession No. 5661617, 2018, pp. 4.

Budin. N. et al., "Efficient synthesis of the ketone body ester (R)-3-hydroxybutyryl-(R)-3-hydroxybutyrate and its (S, S) enantiomer," Bioorganic Chemistry, vol. 80, Oct. 2018, pp. 560-564.

Huang Dexiang, "Clinical Parenteral nutrition", Jan. 31, 1994, pp. 1-20.

Kaster M.P. et al, "Caffeine acts through neuronal adenosine A2A receptors to prevent mood and memory dysfunction triggered by chronic stress", Proceedings of the National Academy of Sciences, vol. 112, No. 25, Jun. 8, 2015, pp. 7833-7838.

Lonza, Duocap Capsules, Feb. 16, 2018, https://web.archive.org/web/20180216001656/https://www.capsugel.com/consumer-health-nutrition-products/duocap-capsules (Year: 2018).

Luis Villasenor, "Supplements and Ketogenic Diets—Facts and Myths", Retrieved from https://www.ketogains.com/2015/09/supplements-and-ketogenic-diets-facts-and-myths/, Sep. 18, 2015, pp. 15.

Lytra. G. et al., "Distribution and Organoleptic Impact of Ethyl 3-Hydroxybutanoate Enantiomers in Wine," J. Agric. Food Chem, vol. 63, Issue 48, 2015, pp. 10484-10491.

Mangels D.R. et al., "Catechins as Potential Mediators of Cardiovascular Health", Translational Sciences, vol. 37, No. 5, May 1, 2017, pp. 757-763.

\* cited by examiner

BETA-HYDROXYBUTYRATE MIXED SALT COMPOSITIONS AND METHODS OF USE

CROSS-REFERENCE TO RELATED APPLICATIONS

This Application is a continuation of U.S. patent application Ser. No. 17/198,634, filed Mar. 11, 2021, which is a continuation of U.S. patent application Ser. No. 16/996,509, filed Aug. 18, 2020, now U.S. Pat. No. 10,973,786, and also a continuation of U.S. patent application Ser. No. 16/720,211, filed Dec. 19, 2019, now U.S. Pat. No. 11,020,362, which is a division of U.S. patent application Ser. No. 16/272,145, filed Feb. 11, 2019, now U.S. Pat. No. 10,736,861, which is a continuation-in-part of U.S. patent application Ser. No. 15/454,157, filed Mar. 9, 2017, now U.S. Pat. No. 10,292,952, which claims the benefit of U.S. Provisional Patent Application No. 62/307,203, filed Mar. 11, 2016, which are incorporated herein by reference in their entirety.

BACKGROUND

1. Field of Disclosure

This disclosure relates to the use of exogenous ketones and ketogenic precursors to quickly produce elevated and sustained levels of ketone bodies in the blood and methods for assisting the body's transition into nutritional ketosis. Specifically, compositions and methods are disclosed which promote, enhance, and/or sustain ketosis in a mammal without contributing to or aggravating an electrolyte imbalance, and in at least some circumstances, helping to restore electrolyte balance.

2. Related Technology

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation of ketone bodies for energy. Ketone bodies can be used by almost all cells of the body as a replacement fuel to satisfy the body's energy needs, including the needs of the brain and heart. During a prolonged fast, for example, blood ketone levels will increase to as high as 2 or 3 mmol/L or more. It is conventionally understood that when blood ketones rise above 0.5 mmol/L, the heart, brain and peripheral tissues are using ketone bodies (beta-hydroxybutyrate and acetoacetate) as the primary fuel source. This condition is referred to as ketosis, or between 1.0 mmol/L and 3.0 mmol/L is called "nutritional ketosis."

Upon transitioning into ketosis, or in other words, during ketogenic metabolism in the liver, the body uses dietary and bodily fats as its primary energy source. Consequently, once in ketosis, one can induce loss of body fat by controlling dietary fat intake and adjusting carbohydrate intake low enough to sustain ketosis.

While in ketosis, the body is in ketogenisis and essentially burning fat for its primary fuel. The body begins cleaving fats into fatty acids and glycerol and transforms the fatty acids into acetyl CoA molecules, which are then eventually transformed through ketogenisis into the water-soluble ketone bodies beta-hydroxybutyrate ((3-hydroxybutyrate or "BHB"), acetoacetate (also known as acetylacetonate), and acetone in the liver. Beta-hydroxybutyrate and acetoacetate are the ketone bodies used by the body for energy while acetone is removed as a by-product of ketogenesis.

The metabolism of ketone bodies is also associated with other beneficial effects, including anticonvulsant effects, enhanced brain metabolism, neuroprotection, muscle sparing properties, and improved cognitive and physical performance. Science-based improvements in efficiency of cellular metabolism, managed through ketone supplementation, can have beneficial impacts on physical, cognitive health, psychological health, and a long-term impact on health with respect to the common avoidable diseases such as obesity, cardiovascular disease, neurodegenerative diseases, diabetes, and cancer.

Despite the many health advantages to pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to entering ketosis through depleting glucose stores in the body is through fasting combined with exercise. This is physically and emotionally demanding and is extremely challenging even for the most motivated and disciplined.

Additionally, the transition into ketosis is often accompanied by hypoglycemia which can cause lethargy and light-headedness in many, resulting in an uncomfortable physiological and mental state commonly referred to as the "low-carb flu." In addition, many people experience a down regulation in their metabolism as the body goes into an "energy-saving" mode. Some suggest that these transitory symptoms may last as long as two to three weeks. During this transition period, if any meal or snack consisting of carbohydrates over the restrictive amount is consumed, there is an immediate termination of ketogenisis exiting the E body from its state of ketosis as the body shifts back to glucose utilization for its primary fuel and the transition into ketosis must begin anew.

If a subject is successful in establishing ketosis, the act of sustaining ketosis is likewise if not a more difficult challenge due to the need to maintain a rigid dietary ratio of carbohydrates and protein to fats. It is further complicated by the disruption of normal electrolyte balances that often occurs when transitioning into and maintaining a ketogenic state. The depletion and lowering of glycogen stores in the liver and muscles lessens the ability of the body to retain water, leading to more frequent urination, and accordingly, a greater loss of electrolytes. Further, the drop in insulin levels caused by ketosis effects the rate at which certain electrolytes are extracted by the kidneys, additionally lowering electrolyte levels in the body.

Such electrolyte imbalances can lead to fatigue, muscle cramping, headaches, dizziness, depression, constipation, skin problems, muscle weakness, and irritability, exacerbating the other detrimental mental and physiological effects often associated with entering and maintaining a ketogenic state, and further increasing the difficulty of promoting and/or sustaining ketosis.

In addition, in more extreme cases, electrolyte imbalances can lead to very serious health problems, such as heart palpitations, respiratory depression, involuntary muscle spasms, and cardiac arrhythmia.

Accordingly, there is a long felt and continuing need for compositions and methods for promoting and/or sustaining ketosis without causing or aggravating detrimental effects associated with ketosis.

BRIEF SUMMARY

Certain embodiments disclosed herein are directed to ketogenic compositions formulated for inducing and/or sustaining ketosis in a subject while simultaneously promoting or maintaining a beneficial electrolytic balance. For example, one or more ketogenic compositions described herein may function to induce and/or sustain ketosis in the subject to which the composition is administered without delivering too much total electrolyte to the body, or too much of a particular electrolyte that may be unhealthy, such as sodium and/or calcium (i.e., so as to not exceed the RDA for a particular electrolyte or only exceed it by a predetermined amount). This allows the ketogenic compositions to induce or sustain ketosis while simultaneously limiting, preventing, or improving an electrolyte imbalance in the subject.

In some embodiments, a ketogenic composition for promoting and/or sustaining ketosis in a subject includes a beta-hydroxybutyrate ((3-hydroxybutyrate or "BHB") mixed salt formed from at least four different cations and comprising 10-70% by weight of sodium BHB, 10-70% by weight of potassium BHB, 10-70% by weight of calcium BHB, and 10-70% by weight of magnesium BHB. Other cations, such as cations provided by organic compounds, such as amines or amino acids, can form compounds or complexes with BHB. Using organic E cations permits higher dosing of BHB without causing electrolyte imbalances or overload.

In some embodiments, a ketogenic composition for promoting and/or sustaining ketosis in a subject includes a plurality of salts formulated from at least four different cations and a single anion, wherein the single anion is BHB, and wherein other anions are omitted from the plurality of salts, the cations being formulated so as to provide a biologically balanced set of cationic electrolytes upon administration to the subject.

In some embodiments, a ketogenic composition for promoting and/or sustaining ketosis in a subject includes: a potassium BHB salt; a sodium BHB salt included in an amount, by weight, that is no greater than an amount, by weight, of the potassium BHB salt; a magnesium BHB salt; and a calcium BHB salt included in an amount, by weight, that is no greater than an amount, by weight, of the magnesium BHB salt.

Some embodiments additionally include one or more transition metal BHB salts, such as zinc BHB or iron BHB. They may also include BHB-amino acid salts.

By limiting the total quantity of sodium and/or calcium BHB salts or any other total quantity of single cationic electrolytes or metal or amino acids in the ketogenic composition (e.g., by including higher amounts of potassium BHB, magnesium BHB, one or more transition metal BHB salts, and/or one or more BHB-amino acid salts), it is possible to substantially increase the total quantity of BHB delivered to the body without delivering an excessive or unhealthy quantity of cationic electrolytes or metal or amino acids (e.g., sodium and/or calcium cations to the body).

The BHB compound can be provided as a racemic mixture of enantiomers, or DL-beta hydroxybutyrate, which can be made synthetically. In humans, the enantiomer D-3-hydroxybutyrate ("D-beta hydroxybutyrate" or "D-BHB") is synthesized in the liver from acetoacetate, the first ketone produced in the fasting. Therefore, it may be desirable to provide BHB as the enantiomer D-3-hydroxybutyrate to increase potency, either enriched relative to L-3-hydroxybutyrate ("L-beta hydroxybutyrate" or "L-BHB") or isolated from L-3-hydroxybutyrate. D-3-hydroxybutyrate is also referred to as "R-beta-hydroxybutyrate".

Some embodiments additionally include a nutritionally acceptable amount of vitamin $D_3$. For example, a composition may include vitamin $D_3$ such that a daily dosage amount of the composition includes vitamin $D_3$ in an amount ranging from about 200 IU to about 8000 IU, or about 400 IU to about 4000 IU, or about 600 IU to about 3000 IU.

In some embodiments, a ketogenic composition is useful as a weight loss supplement, as a treatment for high blood glucose or type II diabetes, as a brain tonic, athletic performance enhancer, as a preventative against metabolic dysfunction, mitochondrial defect, insulin resistance, as an adjunct to a ketogenic diet, as an anti-aging supplement, and for other uses associated with improved metabolic health.

In preferred embodiments, the ketogenic composition is provided as a solid or powder form as opposed to a liquid or gel form. Such solid-form ketogenic compositions, in addition to providing the beneficial ketogenic effects and beneficial electrolytic effects described herein, are preferably also formulated so as to provide for sufficient ease of handling and manufacturability. Alternatively, the composition may be in the form of a liquid mouth spray for fast delivery and uptake. In some embodiments, the beneficial ketogenic and electrolytic effects are realized without hampering or overly impacting the manufacturability or ease of handling of the composition.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

Definitions

The compound "beta-hydroxybutyrate," also known as β-hydroxybutyrate, 3-hydroxybutyrate, βHB, BHB, or beta-hydroxybutyrate, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure shown below represents beta-hydroxybutyrate compounds that may be utilized in the disclosed compositions:

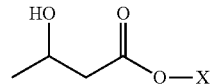

where, X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

Beta-hydroxybutyrate can be utilized by a patient's body as a fuel source during instances of low glucose levels in the subject or when a patient's body is supplemented with a usable form of beta-hydroxybutyrate. Beta-hydroxybutyrate is commonly referred to as a "ketone body" although not technically a ketone.

As used herein, "ketogenic composition" refers to a composition including a mixed BHB salt. The ketogenic composition is formulated to induce and/or sustain ketosis in a subject to which it is administered while simultaneously promoting electrolytic benefits in the subject.

The term "mixed salt" or "multi-salt" is used herein to describe the portion of a ketogenic composition comprising the multiple BHB salts. The mixed BHB salts include at least four separate cation forms of BHB salt, and the salts are relatively proportioned to promote electrolytic benefits in the subject.

As used herein, "subject" or "patient" refers to members of the animal kingdom, including mammals, such as but not limited to, humans and other primates; rodents, fish, reptiles, and birds. The subject may be any animal requiring therapy, treatment, or prophylaxis, or any animal suspected of requiring therapy, treatment, or prophylaxis. Prophylaxis means that regiment is undertaken to prevent a possible occurrence, such as where a high glucose or diabetes is identified. "Patient" and "subject" are used interchangeably herein.

The term "unit dose" refers to a dosage form that is configured to deliver a specified quantity or dose of composition or component thereof. Example dosage forms include, but are not limited to, tablets, capsules, powders, food products, food additives, beverages, beverage additives, candies, suckers, pastilles, food supplements, sprays, injectables, and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, syringe, dropper, spoon, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

"Ketosis" as used herein refers to a subject having blood ketone levels within the range of about 0.5 mmol/L and about 16 mmol/L in a subject. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis."

The term "medium chain triglycerides" (MCT) refers to molecules having a glycerol backbone attached to three medium chain fatty acids. Medium chain fatty acids range from 6 to 12 carbon atoms in length, e.g., 8 to 10 carbon atoms in length. Exemplary fatty acids are caprylic acid, also known as octanoic acid, comprising 8 carbon molecules, and capric acid, also known as decanoic acid, comprising 10 carbon molecules. Because MCTs are ketone body precursors, including one or more MCTs may provide an additional source for the production of ketone bodies independent of the BHB-salts, thus helping to mitigate the risk of consuming too many electrolytes in elevating ketone levels to a desired therapeutic level.

In addition, the composition may comprise at least one short chain fatty acid, or a mono-, di- or triglyceride, or other ester of the at least one short chain fatty acid, having fewer than 6 carbons and/or at least one long chain fatty acid, or a mono-, di- or triglyceride of the at least one long chain fatty acid, having more than 12 carbons.

Examples of short chain fatty acids include acetic acid, propionic acid, butyric acid, isobutyric acid, valeric acid, and isovaleric acid. Examples of medium chain fatty acids include caproic acid, caprylic acid, capric acid, and lauric acid. Examples of long-chain fatty acids include myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids.

The term "administration" or "administering" is used herein to describe the process in which the mixed salt ketogenic compositions are delivered to a subject. The composition may be administered in various ways including oral, intragastric, and parenteral (referring to intravenous and intra-arterial and other appropriate parenteral routes), among others.

II. Mixed Salt Ketogenic Compositions

The administration of BHB results in elevated and sustained blood levels of ketone bodies, thereby exploiting the metabolic and physiological advantages of sustained ketosis. Raising the levels of ketone bodies in the blood provides a subject with greater flexibility in diet options as compared to a method that aims to induce and sustain ketosis based on diet alone (e.g., based on fasting and/or limited carbohydrate intake). For example, a subject that has been administered an appropriate amount of BHB will be able to eat an occasional carbohydrate or sugar-based food without jeopardizing the ketogenic state and shifting back into a glucose-based metabolic state. Further, such administration facilitates easier transitioning into a ketogenic state while reducing or eliminating the detrimental effects typically associated with entering ketosis.

Subjects entering or maintaining a ketogenic state will often be in a state of electrolyte imbalance due to the metabolic shifts involved with ketosis, including enhanced diuretic effects and changes in insulin profiles. Thus, while there are many benefits to the administration of BHB in order to promote or sustain ketosis in a subject, the resulting electrolyte imbalance, and its associated detrimental physiological effects can offset the benefits of ketosis and/or make it more difficult for a subject to maintain ketosis at the desired levels or for a desired length of time.

Further, because BHB may typically be administered in salt form, where one or more BHB molecules are the anions to a selected cation, the introduction of additional cation electrolytes can exacerbate the electrolyte imbalance of the subject. For example, a formulation having an overly high level and/or an overly high proportion of a particular form of BHB salt can cause further electrolyte imbalance and/or cause other detrimental health effects. In some circumstances, even if the particular form of BHB salt eases an electrolyte imbalance to some degree, it can introduce other negative and undesirable health effects.

By way of example, a formulation having an overly high level and/or an overly high proportion of sodium BHB compounds will increase levels of sodium in the subject. While sodium is a necessary nutrient, having levels that are outside of optimal ranges can lead to detrimental effects. High levels of sodium are associated with hypertension and poor cardiovascular health. In particular, high levels of sodium relative to potassium will promote hypertension and raise the risk of cardiovascular disease.

In another example, a formulation having an overly high level or an overly high proportion of calcium BHB salts will increase calcium levels in the subject. While calcium is also a necessary nutrient, and is particularly important for good bone health, overly high levels of calcium may not be fully absorbed into the bones, and may instead build up in soft tissues, leading to detrimental calcification and hardening of the tissues and raising the risk of heart disease (e.g., associated with hardened arteries), kidney stones, arthritis, and other problematic conditions. In particular, high levels of calcium relative to magnesium can aggravate these negative effects. Magnesium functions by stimulating the hormone calcitonin and functions to convert vitamin D to its active form so it can promote calcium absorption in the bones as opposed to calcium deposition in soft tissues.

The administration of BHB salts in inappropriate amounts and proportions can therefore cause or aggravate detrimental health effects. Further, accounting for imbalances through other dietary options is not always easy or even possible for a subject attempting to maintain a ketogenic state. For example, many of the foods known to have high levels of potassium and/or magnesium, such as whole grains, bananas, avocados, milk, yogurt, oatmeal, corn, peas, potatoes, and squash, contain high levels of carbohydrates and are not compatible with a strict ketogenic diet when consumed in any substantial amount.

Embodiments disclosed herein provide a therapeutically effective amount of BHB in the form of a mixed BHB salt. Beneficially, the mixed BHB salt is formulated to provide a biologically balanced set of cation electrolytes. One or more embodiments therefore provide the advantages of initiating and/or sustaining ketosis while simultaneously promoting positive electrolytic effects. For example, embodiments disclosed herein are capable of promoting ketogenesis without aggravating negative electrolyte imbalances, without promoting other detrimental health effects associated with electrolyte imbalances, and in at least some circumstances, even improving or easing electrolyte imbalances.

In some embodiments, a ketogenic composition includes a BHB mixed salt. The mixed salt includes at least four different cations, and the mixed salt is proportioned such that it comprises 10-70% by weight of each of sodium BHB, potassium BHB, calcium BHB, and magnesium BHB.

In some embodiments, the sodium BHB is included in an amount ranging from about 10% to about 30%, or about 12% to about 25%, or about 14% to about 22%, or about 16% to about 20%, or about 18%, by weight of the mixed salt. In some embodiments, the potassium BHB is included in an amount ranging from about 10% to about 30%, or about 12% to about 25%, or about 14% to about 22%, or about 16% to about 20%, or about 18%, by weight of the mixed salt.

In some embodiments, the calcium BHB is included in an amount ranging from about 10% to about 40%, or about 12% to about 35%, or about 15% to about 30%, or about 18% to about 25%, or about 20% to about 23%, by weight of the mixed salt. In some embodiments, the magnesium BHB is included in an amount ranging from about 10% to about 40%, or about 12% to about 35%, or about 15% to about 30%, or about 18% to about 25%, or about 20% to about 23%, by weight of the mixed salt.

The BHB compound can be provided as a racemic mixture of enantiomers, or DL-beta hydroxybutyrate, which can be made synthetically. In humans, the enantiomer D-3-hydroxybutyrate ("D-beta hydroxybutyrate" or "D-BHB") is synthesized in the liver from acetoacetate, the first ketone produced in the fasting. Therefore, it may be desirable to provide BHB as the enantiomer D-3-hydroxybutyrate to increase potency, either enriched relative to L-3-hydroxybutyrate ("L-beta hydroxybutyrate" or "L-BHB") or isolated from L-3-hydroxybutyrate. D-3-hydroxybutyrate is also referred to as "R-beta-hydroxybutyrate".

In some embodiments, a ketogenic composition additionally includes a therapeutically effective amount of vitamin $D_3$. Vitamin $D_3$ works in conjunction with magnesium and calcium to promote good bone health and to prevent undesirable calcification of soft tissues. In preferred embodiments, vitamin $D_3$ is included in an amount such that an average daily dose of the ketogenic composition includes about 200 IU ("International Units") to about 8000 IU, or about 400 IU to about 4000 IU, or about 600 IU to about 3000 IU of vitamin $D_3$. In some embodiments, vitamin $D_3$ is included in an amount such that an average daily dose of the ketogenic composition includes about 5 μg to about 200 μg, or about 10 μg to about 100 μg, or about 15 μg to about 75 μg of vitamin $D_3$.

Some embodiments include additional BHB salts as part of the mixed salt of the ketogenic composition. For example, some embodiments include one or more transition metal BHB salts. Transition metal cations suitable for use as part of the mixed BHB salt include lithium, chromium, manganese, cobalt, copper, zinc, iron, (e.g., as an iron II or iron III cation), molybdenum, and selenium.

In embodiments where a transition metal BHB salt is included, preferred salts include zinc BHB and iron BHB. Some embodiments include a zinc BHB salt in an amount ranging from about 2% to about 40%, or about 3% to about 30%, or about 4% to about 20%, or about 5% to about 15%, or about 7% to about 13%, by weight of the mixed salt. Some embodiments include an iron BHB salt in an amount ranging from about 2% to about 40%, or about 3% to about 30%, or about 4% to about 20%, or about 5% to about 15%, or about 7% to about 13%, by weight of the mixed salt.

In preferred embodiments, the sodium BHB is included in an amount, by weight, no greater than the amount of the potassium BHB. This can advantageously enable the administration of necessary sodium and potassium electrolytes, providing a beneficial electrolytic effect to the subject, without causing or aggravating any of the unwanted health effects associated with high sodium to potassium ratios (e.g., hypertension, cardiovascular disease, and other unfavorable effects).

In preferred embodiments, the calcium BHB is included in an amount, by weight, no greater than the amount of the magnesium BHB. This can advantageously enable the administration of necessary calcium and magnesium electrolytes, providing a beneficial electrolytic effect to the subject, without causing or aggravating any of the unwanted health effects associated with high calcium to magnesium ratios (e.g., tissue calcification, poor bone health, and other unfavorable effects).

In preferred embodiments, mixed salts can also be formulated such that the molar ratio of sodium ions to potassium ions is no greater than 1, and/or such that the molar ratio of calcium ions to magnesium ions in no greater than 1.

The mixed salt is preferably formulated so that an average daily dose of the ketogenic composition provides an amount of at least one of the cations of the mixed salt that is within a range of about 0.25 to about 10 times the recommended dietary allowance (RDA) of the of the at least one cation, or about 0.5 to 5 times, or about 0.75 to 2 times the RDA of the at least one cation. For example, the mixed salt may be formulated such that when a subject takes a daily amount of the ketogenic composition, the subject will have consumed, through the mixed salt, an amount of the cation electrolyte falling within the foregoing ranges. In some embodiments, the mixed salt is formulated such that the at least one cation electrolyte falling within the foregoing ranges after a daily dose of the ketogenic compound is potassium and/or magnesium.

Of course, in some circumstances RDA levels may be exceeded without necessarily experiencing toxicity or negative health effects. One of skill in the art will understand that in some circumstances, the mixed salt may be formulated such that one or more of the electrolytes is included in an amount that leads to an exceedance of the RDA by more than 10 times the RDA, without necessarily causing detrimental effects.

In alternative embodiments, BHB compositions may include one or more BHB salts in which at least some of the cations are provided by one or more amino acids or other organic compounds that have a net positive charge at the pH at which the BHB salts are produced. BHB-amino acid salts can provide soluble forms of BHB without providing electrolytes, such as sodium, potassium, calcium or magnesium. This permits the manufacture of BHB salts with a reduced quantity of electrolytes and/or a more healthy amount and/or healthier balance of electrolytes, particularly where it is desired to delivered higher quantities of BHB for therapeutic reasons without further increasing electrolyte load. Suitable amino acids for this purpose can include amino acids that contain more than one amine group capable of being protonated to form a compound having a net positive charge, which can provide the counter cation for BHB anion. Examples include arginine, lysine, leucine, iso-leucine, histidine, ornithine, citrulline, L-glutamine, or other suitable amino acids or metabolites of amino acids (e.g., creatine). Some amino acids also provide health benefits. For example, l-arginine can increase nitric oxide in the blood, which dilates blood vessels and improves blood circulation for persons with heart conditions (and may help men suffering from erectile dysfunction).

In some embodiments, a ketogenic composition may also include other ketone body precursors, such as one or more medium chain fatty acids or one or more mono-, di-, or triglycerides of one or more medium chain fatty acids. Including one or more medium chain fatty acids, or a mono-, di-, or triglyceride of one or more medium chain fatty acids can provide an additional source for the production of ketone bodies independent of the BHB-salts. In other words, the BHB salts promote fast achievement of ketosis in the body while the medium chain fatty acid or a mono-, di-, or triglyceride of a medium chain fatty acid helps sustain the body in a state of ketosis when the BHB salts have already been consumed by the body. Including at least one of an MCT, medium chain fatty acid, or a mono-, di-, or triglyceride of a medium chain fatty acid can help sustain ketosis over a longer period of time without having to provide more BHB-salts, which can be particularly beneficial when the amount of BHB salts otherwise required for extended ketosis contain too high of a quantity of electrolytes. The at least one medium chain fatty acid preferably has from 6 to 12 carbons, more preferably from 8 to 10 carbons. Compositions and methods related to the combination of BHB with a medium chain fatty acid, or ester thereof, are disclosed in U.S. Pat. No. 9,138,420, which patent is incorporated herein by this reference in its entirety.

Examples and sources of the medium chain fatty acid, or an ester thereof such as a medium chain triglyceride, include coconut oil, coconut milk powder, fractionated coconut oil, palm oil, palm kernel oil, isolated medium chain fatty acids, such as isolated hexanoic acid (i.e, caproic acid), isolated octanoic acid (i.e., caprylic acid), isolated decanoic acid (i.e., capric acid), and lauric acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

As discussed elsewhere, the compositions may also include short chain fatty acids, such as butyric acid, isobutyric acid, valeric acid, isovaleric acid, propionic acid, lactic acid, acetic acid, and the like.

Notwithstanding the foregoing, there is a practical limit to how much MCT or other medium chain fatty acid source an individual can take, with some individuals having lower tolerance for MCT or other medium chain fatty acid sources (e.g., they may cause gastrointestinal issues). The ability of the mixed BHB salts to provide a substantial increase in the amount of BHB delivered without providing excessive electrolyte loading, particularly excessive loading of certain electrolytes that are not healthy in high dosages, such as sodium and calcium ions, permits a person to sustain a high level of ketosis for a longer period of time without having to also consume an excessive quantity of MCT or other medium chain fatty acid source.

Some embodiments also include one or more additional ketone precursors or supplements. These additional ketone precursors or supplements might include acetoacetate, ketone esters, and/or other compounds that cause a rise in blood ketone levels without adding more electrolytes to the bloodstream.

In some embodiments, the ketogenic composition may be provided as a solid or powder form as opposed to a liquid or gel form. Such solid-form ketogenic compositions, in addition to promoting beneficial ketogenic effects and electrolytic effects described herein, are formulated so as to provide for sufficient ease of handling and manufacturability. For example, in a mixed salt formulation of various BHB salts, certain BHB salts will exhibit different material properties (e.g., hygroscopicity) and the relative amounts of the different salts in the mixed salt formulation will therefore affect the overall properties of the composition.

In an alternative embodiment, the ketogenic composition may be provided as a liquid, such as in the form of a shot or mouth spray for fast delivery and absorption. Liquid forms may include one or more liquid carriers, such as water, ethanol, glycerin, propylene glycol, 1, 3-propandiol, and the like, into which the mixed BHB salts are dissolved or dispersed. The composition may include flavoring agents that help mask the otherwise poor taste of BHB salts. These include essential oils, such as peppermint, natural and artificial sweeteners, and other flavorants known in the art.

Manufacturing of the mixed salt formulations described herein has demonstrated that certain BHB salts, in particular potassium BHB and magnesium BHB, exhibit greater hygroscopicity than other BHB salts. Improperly proportioning the BHB salts has been shown to create "sticky" formulations that do not flow or handle well, increasing manufacturing costs and potentially decreasing the shelf-life, stability and efficacy of the ketogenic composition product.

Accordingly, one or more of the compositions described herein are formulated and balanced so as to provide the ketogenic and electrolytic benefits and advantages described above, while at the same time not unduly or unacceptably resulting in material properties that overly hamper or disrupt manufacturability of the salt. In particular, at least some embodiments include different BHB salts in proportions that provide sufficient calcium BHB and sodium BHB (which typically promote manufacturability and handling) without overly including these salts at overly high levels which promote harmful health effects. Likewise, at least some embodiments include potassium BHB and magnesium BHB (which typically hampers manufacturability and handling) in amounts sufficient to balance the calcium BHB but not in overly excessive amounts, which unduly increases manufacturing difficulty.

In some embodiments, ketogenic compositions may further include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), phosphate salt (e.g., tricalcium phosphate), talcum, powdered cellulose, and the like.

III. Administration

Ketogenic compositions described herein may be administered to a subject in therapeutically effective dosages and/or in frequencies to induce or sustain ketosis. In some embodiments, a single dose will include an amount of BHB mixed salt ranging from about 1 to about 50 grams, or about 2 to about 40 grams, or about 5 to about 30 grams, or about 10 to about 20 grams.

In some embodiments, the ketogenic compositions can include or be administered together with other supplements, such as vitamin $D_3$.

In some embodiments, the compositions may further include one or more medium chain fatty acids, fatty acid esters, or mono-, di- or triglycerides of medium chain fatty acids in order to provide an additional source of ketone bodies, as discussed elsewhere, for sustaining ketosis for a longer period of time compared to if just the BHB salts were used by themselves. In some embodiments, the composition is preferably administered such that the ratio of BHB to medium chain fatty acid (or ester thereof) ranges from about 4:1 to about 1:4, or from about 2:1 to about 1:2, or from about 1.5:1 to about 1:1.5.

In some embodiments, the subject preferably follows a ketogenic diet that restricts intake of carbohydrates and protein during the period of administration of the composition. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In a preferred embodiment, a ketogenic composition is administered via oral administration of the composition in a solid and/or powdered form, such as in a powdered mixture (e.g., powder filled gelatin capsules), hard-pressed tablets, or other oral administration route known to those skilled in the art.

In some embodiments, multiple doses of the composition are administered. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etc.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of the BHB salts and/or corresponding electrolytes, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once, or may be divided and administered over intervals of time. It is to be understood that administration may be adjusted according to individual need and professional judgment of a person administrating or supervising the administration of the compositions.

IV. EXAMPLES

The following is a description of exemplary BHB mixed salt compositions and other ketogenic compositions useful for inducing and/or sustaining a ketogenic state in a subject to which they are administered while simultaneously providing a balanced set of cationic electrolytes.

Example 1

A BHB mixed salt is prepared by mixing sodium BHB at 23% by weight, potassium BHB at 23% by weight, calcium BHB at 27% by weight, and magnesium BHB at 27% by weight. The BHB mixed salt is readily administered as a ketogenic composition, such as in powder form as a dietary supplement mixed with food or drink, in the form of one or more capsules or tablets, or in liquid form such as a mouth spray.

Example 2

A BHB mixed salt is prepared by mixing sodium BHB at 18% by weight, potassium BHB at 18% by weight, calcium BHB at 32% by weight, and magnesium BHB at 32% by weight. The BHB mixed salt is readily administered as a ketogenic composition, such as in powder form as a dietary supplement mixed with food or drink, in the form of one or more capsules or tablets, or in liquid form such as a mouth spray.

Example 3

A BHB mixed salt is prepared by mixing sodium BHB at 15% by weight, potassium BHB at 20% by weight, calcium BHB at 30% by weight, and magnesium BHB at 35% by weight. Vitamin $D_3$ is added in an amount of 800 IU for every 20 grams of the BHB mixed salt (representing an average daily dose). The BHB mixed salt is readily administered as a ketogenic composition, such as in powder form as a dietary supplement mixed with food or drink, in the form of one or more capsules or tablets, or in liquid form such as a mouth spray.

Example 4

A BHB mixed salt is prepared by mixing sodium BHB at 15% by weight, potassium BHB at 15% by weight, calcium BHB at 35% by weight, and magnesium BHB at 35% by weight. The BHB mixed salt is readily administered as a ketogenic composition, such as in powder form as a dietary supplement mixed with food or drink, in the form of one or more capsules or tablets, or in liquid form such as a mouth spray.

Example 5

A BHB mixed salt is prepared by mixing sodium BHB at 30% by weight, potassium BHB at 30% by weight, calcium BHB at 20% by weight, and magnesium BHB at 20% by weight. Vitamin $D_3$ is added in an amount of 1200 IU for every 15 grams of the BHB mixed salt (representing an average daily dose). The BHB mixed salt is readily administered as a ketogenic composition, such as in powder form as a dietary supplement mixed with food or drink, in the form of one or more capsules or tablets, or in liquid form such as a mouth spray.

Example 6

A BHB mixed salt is prepared by mixing sodium BHB at 15% by weight, potassium BHB at 15% by weight, calcium BHB at 18% by weight, magnesium BHB at 18% by weight, zinc BHB at 17% by weight, and iron BHB at 17% by weight. The BHB mixed salt is readily administered as a ketogenic composition, such as in powder form as a dietary supplement mixed with food or drink, in the form of one or more capsules or tablets, or in liquid form such as a mouth spray.

Example 7

A BHB mixed salt is prepared by mixing sodium BHB at 20% by weight, potassium BHB at 20% by weight, calcium BHB at 20% by weight, magnesium BHB at 20% by weight, and zinc BHB at 20% by weight. The BHB mixed salt is readily administered as a ketogenic composition, such as in powder form as a dietary supplement mixed with food or drink, in the form of one or more capsules or tablets, or in liquid form such as a mouth spray.

Example 8

A BHB mixed salt is prepared by mixing sodium BHB at 15% by weight, potassium BHB at 25% by weight, calcium BHB at 20% by weight, magnesium BHB at 25% by weight, and iron BHB at 15% by weight. The BHB mixed salt is readily administered as a ketogenic composition, such as in powder form as a dietary supplement mixed with food or drink, in the form of one or more capsules or tablets, or in liquid form such as a mouth spray.

Example 9

A BHB mixed salt is prepared by mixing sodium BHB at 15% by weight, potassium BHB at 15% by weight, calcium BHB at 20% by weight, magnesium BHB at 20% by weight, zinc BHB at 20% by weight, and iron BHB at 10% by weight. Vitamin $D_3$ is added in an amount of 600 IU for every 10 grams of the BHB mixed salt (representing an average daily dose). The BHB mixed salt is readily administered as a ketogenic composition, such as in powder form as a dietary supplement mixed with food or drink, in the form of one or more capsules or tablets, or in liquid form such as a mouth spray or shot.

Example 10

A BHB mixed salt is prepared by mixing sodium BHB at 23% by weight, potassium BHB at 23% by weight, calcium BHB at 27% by weight, and magnesium BHB at 27% by weight. The BHB mixed salt is readily administered as a ketogenic composition, such as in powder form as a dietary supplement mixed with food or drink, in the form of one or more capsules or tablets, or in liquid form such as a mouth spray.

Example 11

A BHB mixed salt is prepared by mixing sodium BHB at 25% by weight, potassium BHB at 25% by weight, calcium BHB at 25% by weight, and magnesium BHB at 25% by weight. The BHB mixed salt is then mixed with an anticaking agent, which is safe for human consumption, at a ratio of 4 to 1 to form a ketogenic composition readily administered to a subject, such as in powder form as a dietary supplement mixed with food or drink, or in the form of one or more capsules or tablets.

Example 12

Any of the foregoing BHB mixed salts is combined with at least one medium chain fatty acid source selected from a medium chain triglyceride, medium chain fatty acid, monoglyceride of a medium chain fatty acid, diglyceride of a medium chain fatty acid, or triglyceride of a medium chain fatty acid having 8 to 10 carbons to provide a ketogenic composition that provides prolonged ketosis over a greater period of time than would be provided by a given dosage of BHB mixed salt by itself. The ratio of medium chain fatty acid source to BHB salts is 4:1, 3:1, 2:1, 1:1 or 1:2.

Example 13

Any of the foregoing BHB mixed salts includes one or more BHB salts of a cationic amino acid selected from arginine, lysine, leucine, iso-leucine, histidine, ornithine, citrulline, L-glutamine, or metabolite of an amino acid, such as creatine). The BHB-amino acid salt decreases the ratio of electrolytes to BHB anions in the composition.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A composition for increasing ketone level in a subject, comprising:
    a plurality of beta-hydroxybutyrate salts comprised of:
        at least one beta-hydroxybutyrate salt selected from:
            calcium beta-hydroxybutyrate; and
            magnesium beta-hydroxybutyrate; and
        at least one other beta-hydroxybutyrate salt selected from:
            sodium beta-hydroxybutyrate;
            potassium beta-hydroxybutyrate;
            calcium beta-hydroxybutyrate; and
            magnesium beta-hydroxybutyrate; and
        at least one additional ketone body or ketone precursor selected from the group consisting of acetoacetate, ketone ester, amino acid salt of beta-hydroxybutyrate, and other ketone body or ketone precursor that causes a rise in blood ketone level without adding more electrolytes to the subject's bloodstream,
    wherein the composition is free of medium chain fatty acids having 6 to 12 carbons and glycerides or other esters thereof.

2. The composition of claim 1, wherein the other ketone body or ketone precursor that causes a rise in blood ketone level without adding more electrolytes to the subject's bloodstream is beta-hydroxybutyric acid.

3. The composition of claim 1, wherein the other ketone body or ketone precursor that causes a rise in blood ketone level without adding more electrolytes to the subject's bloodstream is not a ketone body ester or acetoacetate.

4. The composition of claim 1, wherein the other ketone body or ketone precursor that causes a rise in blood ketone level without adding more electrolytes to the subject's bloodstream is acetoacetate.

5. The composition of claim 1, wherein the plurality of beta-hydroxybutyrate salts are characterized by at least one of:
    10% to 70% by weight of calcium beta-hydroxybutyrate;
    10% to 70% by weight of magnesium beta-hydroxybutyrate;
    10% to 70% by weight of sodium beta-hydroxybutyrate; or
    10% to 70% by weight of potassium beta-hydroxybutyrate.

6. The composition of claim 1, wherein the composition comprises a greater total weight of calcium and magnesium beta-hydroxybutyrate salts than a total weight of sodium and potassium beta-hydroxybutyrate salts.

7. The composition of claim 1, wherein the composition comprises at least 20% by total weight of calcium beta-hydroxybutyrate and/or magnesium beta-hydroxybutyrate.

8. The composition of claim 1, wherein the composition comprises calcium beta-hydroxybutyrate, magnesium beta-hydroxybutyrate, and at least one of sodium beta-hydroxybutyrate or potassium beta-hydroxybutyrate.

9. The composition of claim 1, wherein the composition comprises calcium beta-hydroxybutyrate and magnesium beta-hydroxybutyrate.

10. The composition of claim 9, wherein the composition further comprises at least one of sodium beta-hydroxybutyrate or potassium beta-hydroxybutyrate.

11. The composition of claim 1, further comprising at least one of vitamin, lithium, chromium, manganese, cobalt, copper, zinc, iron, molybdenum, selenium, amino acid, flavoring agent, essential oil, natural sweetener, artificial sweetener, or other supplement.

12. The composition of claim 1, further comprising at least one of anticaking agent, flow agent, moisture absorber, aluminosilicate, ferrocyanide, carbonate salt, bicarbonate salt, silicate, phosphate, talcum, or powdered cellulose.

13. A composition for increasing ketone level in a subject, comprising:
    a plurality of beta-hydroxybutyrate salts comprising calcium beta-hydroxybutyrate, magnesium beta-hydroxybutyrate, and optionally at least one of:
        sodium beta-hydroxybutyrate; or
        potassium beta-hydroxybutyrate; and
    at least one additional ketone body or precursor selected from the group consisting of acetoacetate, ketone ester, amino acid salt of beta-hydroxybutyrate, and other ketone body or ketone precursor that causes a rise in blood ketone level without adding more electrolytes to the subject's bloodstream,
    wherein the composition is free of medium chain fatty acids having 6 to 12 carbons and glycerides or other esters thereof.

14. The composition of claim 13, wherein the beta-hydroxybutyrate salts comprise:
    calcium beta-hydroxybutyrate;
    magnesium beta-hydroxybutyrate; and
    at least one other beta-hydroxybutyrate salt selected from:
        sodium beta-hydroxybutyrate;
        potassium beta-hydroxybutyrate; and
        amino acid salts of beta-hydroxybutyrate.

15. The composition of claim 14, wherein the beta-hydroxybutyrate salts comprise at least 20% by total weight of calcium beta-hydroxybutyrate and/or magnesium beta-hydroxybutyrate.

16. The composition of claim 14, wherein the beta-hydroxybutyrate salts comprise at least 30% by combined weight of calcium beta-hydroxybutyrate and magnesium beta-hydroxybutyrate.

17. The composition of claim 16, wherein the beta-hydroxybutyrate salts further comprise at least one of sodium beta-hydroxybutyrate or potassium beta-hydroxybutyrate.

18. The composition of claim 1, wherein the composition comprises only one of calcium beta-hydroxybutyrate or magnesium beta-hydroxybutyrate.

19. The composition of claim 14, wherein the composition comprises only one of sodium beta-hydroxybutyrate or potassium beta-hydroxybutyrate.

20. A composition for increasing ketone level in a subject, comprising:
   at least three beta-hydroxybutyrate salts selected from:
      calcium beta-hydroxybutyrate;
      magnesium beta-hydroxybutyrate;
      sodium beta-hydroxybutyrate; and
      potassium beta-hydroxybutyrate;
   at least one additional ketone body or precursor selected from the group consisting of acetoacetate, ketone ester, amino acid salt of beta-hydroxybutyrate, and other ketone body or ketone precursor that causes a rise in blood ketone level without adding more electrolytes to the subject's bloodstream; and
   at least one of vitamin, lithium, chromium, manganese, cobalt, copper, zinc, iron, molybdenum, selenium, amino acid, flavoring agent, essential oil, natural sweetener, artificial sweetener, or other supplement,
   wherein the composition is free of medium chain fatty acids having 6 to 12 carbons and glycerides or other esters thereof.

21. The composition of claim 1, further comprising at least one short chain fatty acid having fewer than 6 carbons, or a mono-, di- or triglyceride, or other ester of the at least one short chain fatty acid.

22. The composition of claim 13, further comprising at least one short chain fatty acid having fewer than 6 carbons, or a mono-, di- or triglyceride, or other ester of the at least one short chain fatty acid.

23. The composition of claim 20, further comprising at least one short chain fatty acid having fewer than 6 carbons, or a mono-, di- or triglyceride, or other ester of the at least one short chain fatty acid.

* * * * *